(12) United States Patent
Cook

(10) Patent No.: US 6,581,604 B2
(45) Date of Patent: *Jun. 24, 2003

(54) LOW-DENSITY POLYETHYLENE DENTAL APPLIANCE AND MOUTHGUARD

(75) Inventor: William A. Cook, Lakeville, MN (US)

(73) Assignee: Bite Tech, Inc., Lakeville, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/827,767

(22) Filed: Apr. 6, 2001

(65) Prior Publication Data

US 2002/0144686 A1 Oct. 10, 2002

(51) Int. Cl.[7] ................................................ A61C 5/14
(52) U.S. Cl. .................... 128/859; 128/861; 128/862
(58) Field of Search ................................ 128/846, 848, 128/859–862; 433/6, 48, 214; 602/902

(56) References Cited

U.S. PATENT DOCUMENTS

| | | |
|---|---|---|
| 257,038 A | 4/1882 | McMann |
| 1,117,928 A | 11/1914 | Thurmond |
| 1,323,832 A | 12/1919 | Chige |
| 1,461,209 A | 7/1923 | Bridges |
| 1,470,888 A | 10/1923 | Smedley |
| 1,487,392 A | 3/1924 | Lee |
| 2,118,980 A | 5/1938 | Montgomery et al. |
| 2,257,709 A | 9/1941 | Anderson |
| 2,423,005 A | 6/1947 | Chaiken |
| 2,630,117 A | 3/1953 | Coleman |
| 2,643,652 A | 6/1953 | Cathcart |
| 2,659,366 A | 11/1953 | Savarese |
| 2,669,988 A | 2/1954 | Carpenter |
| 2,678,043 A | 5/1954 | Stark |
| 2,694,397 A | 11/1954 | Herms |
| 2,702,032 A | 2/1955 | Freedland |
| 2,708,931 A | 5/1955 | Freedland |

(List continued on next page.)

FOREIGN PATENT DOCUMENTS

| | | |
|---|---|---|
| CA | 1147583 | 6/1983 |
| DE | 480423 | 7/1929 |

OTHER PUBLICATIONS

Mouth Protectors: Give Your Teeth a Sporting Chance, American Dental Association, 1985.

Stephen D. Smith, D.M.D., Muscular Strength Correlated to Jaw Posture and the Temporomandibular Joint, New York State Dental Journal, vol. 44, No. 7, Aug.–Sep. 1978.

W.B. May, D.D.S., Reduction of Stress in the Chewing Mechanism—Part III.

*Primary Examiner*—Michael A. Brown
(74) *Attorney, Agent, or Firm*—Gerald E. Helget; Nelson R. Capes; Briggs and Morgan

(57) ABSTRACT

A customizable dental appliance adapted to lie within the mouth of a person consisting of occlusal posterior pads optionally with a connective arch or a u-shaped style base with upstanding labial and/or buccal walls. The appliance is made of low-density polyethylene.

2 Claims, 1 Drawing Sheet

U.S. PATENT DOCUMENTS

| | | |
|---|---|---|
| 2,750,941 A | 6/1956 | Cathcart |
| 2,833,278 A | 5/1958 | Ross |
| 2,847,003 A | 8/1958 | Helmer et al. |
| 2,933,811 A | 4/1960 | Lifton |
| 2,966,908 A | 1/1961 | Cathcart et al. |
| 3,016,052 A | 1/1962 | Zubren |
| 3,058,462 A | 10/1962 | Greenblum |
| 3,073,300 A | 1/1963 | Berghash |
| 3,082,765 A | 3/1963 | Helmer |
| 3,107,667 A | 10/1963 | Moore |
| 3,124,129 A | 3/1964 | Grossberg |
| 3,126,002 A | 3/1964 | Owens |
| 3,203,417 A | 8/1965 | Helmer |
| 3,207,153 A | 9/1965 | Goldstein |
| 3,223,085 A | 12/1965 | Gores et al. |
| 3,247,844 A | 4/1966 | Berghash |
| 3,312,218 A | 4/1967 | Jacobs |
| 3,319,626 A | 5/1967 | Lindsay |
| 3,407,809 A | 10/1968 | Ross |
| 3,411,501 A | 11/1968 | Greenberg |
| 3,416,527 A | 12/1968 | Hoef |
| 3,448,738 A | 6/1969 | Berghash |
| 3,457,916 A | 7/1969 | Wolicki |
| 3,485,242 A | 12/1969 | Greenberg |
| 3,496,936 A | 2/1970 | Gores |
| 3,505,995 A | 4/1970 | Greenberg |
| 3,513,838 A | 5/1970 | Foderick et al. |
| 3,518,988 A | 7/1970 | Gores |
| 3,532,091 A | 10/1970 | Lerman |
| 3,682,164 A | 8/1972 | Miller |
| 3,692,025 A | 9/1972 | Greenberg |
| 3,768,465 A | 10/1973 | Helmer |
| 3,864,832 A | 2/1975 | Carlson |
| 3,916,527 A | 11/1975 | Linkow |
| 3,924,638 A | 12/1975 | Mann |
| 3,943,924 A | 3/1976 | Kallestad et al. |
| 4,030,493 A | 6/1977 | Walters et al. |
| 4,044,762 A | 8/1977 | Jacobs |
| 4,063,552 A | 12/1977 | Going et al. |
| 4,114,614 A | 9/1978 | Kesling |
| 4,185,817 A | 1/1980 | Peterson |
| 4,211,008 A | 7/1980 | Lerman |
| 4,330,272 A | 5/1982 | Bergersen |
| 4,337,765 A | 7/1982 | Zimmerman |
| 4,348,178 A | 9/1982 | Kurz |
| 4,376,628 A | 3/1983 | Aardse |
| 4,457,708 A | 7/1984 | Dufour |
| 4,490,112 A | 12/1984 | Tanaka et al. |
| 4,495,945 A | 1/1985 | Liegner |
| 4,519,386 A | 5/1985 | Sullivan |
| 4,568,280 A | 2/1986 | Ahlin |
| 4,591,341 A | 5/1986 | Andrews |
| 4,640,273 A | 2/1987 | Greene et al. |
| 4,671,766 A | 6/1987 | Norton |
| 4,672,959 A | 6/1987 | May et al. |
| 4,727,867 A | 3/1988 | Knoderer |
| 4,755,139 A | 7/1988 | Abbatte et al. |
| 4,763,791 A | 8/1988 | Halverson et al. |
| 4,765,324 A | 8/1988 | Lake, Jr. |
| 4,791,941 A | 12/1988 | Schaefer |
| 4,793,803 A | 12/1988 | Martz |
| 4,799,500 A | 1/1989 | Newbury |
| 4,810,192 A | 3/1989 | Williams |
| 4,838,283 A | 6/1989 | Lee, Jr. |
| 4,848,365 A | 7/1989 | Guarlotti et al. |
| 4,867,147 A | 9/1989 | Davis |
| 4,920,984 A * | 5/1990 | Furumichi .................. 128/861 |
| 4,944,947 A | 7/1990 | Newman |
| 4,955,393 A | 9/1990 | Adell |
| 4,976,618 A | 12/1990 | Anderson |
| 4,977,905 A | 12/1990 | Kittelsen et al. |
| 4,989,616 A | 2/1991 | Lee, Jr. |
| 5,031,611 A | 7/1991 | Moles |
| 5,031,638 A | 7/1991 | Castaldi |
| 5,063,940 A | 11/1991 | Adell et al. |
| 5,076,785 A | 12/1991 | Tsai |
| 5,082,007 A | 1/1992 | Adell |
| 5,103,838 A | 4/1992 | Yousif |
| 5,112,225 A | 5/1992 | Diesso |
| 5,117,816 A | 6/1992 | Shapiro et al. |
| D328,494 S | 8/1992 | Schwendeman et al. |
| 5,152,301 A | 10/1992 | Kittelsen et al. |
| 5,154,609 A | 10/1992 | George |
| 5,165,424 A | 11/1992 | Silverman |
| 5,174,284 A | 12/1992 | Jackson |
| 5,194,003 A | 3/1993 | Garay et al. |
| 5,194,004 A | 3/1993 | Bergersen |
| 5,203,351 A | 4/1993 | Adell |
| 5,234,005 A | 8/1993 | Kittelsen et al. |
| 5,235,991 A | 8/1993 | Minneman |
| 5,259,762 A | 11/1993 | Farrell |
| 5,277,203 A | 1/1994 | Hays |
| D343,928 S | 2/1994 | Kittelsen |
| 5,293,880 A | 3/1994 | Levitt |
| 5,297,960 A | 3/1994 | Burns |
| 5,299,936 A | 4/1994 | Ueno |
| 5,302,117 A | 4/1994 | Kraut et al. |
| 5,313,960 A | 5/1994 | Tosasi |
| 5,316,474 A | 5/1994 | Robertson |
| 5,320,114 A | 6/1994 | Kittelsen et al. |
| 5,323,787 A | 6/1994 | Pratt |
| 5,328,362 A | 7/1994 | Watson et al. |
| 5,336,086 A | 8/1994 | Simmen et al. |
| 5,339,832 A | 8/1994 | Kittelsen et al. |
| 5,353,810 A | 10/1994 | Kittelsen et al. |
| 5,365,946 A | 11/1994 | McMillan |
| 5,385,155 A | 1/1995 | Kittelsen et al. |
| 5,386,821 A | 2/1995 | Poterack |
| D356,188 S | 3/1995 | Kittelsen |
| 5,401,234 A | 3/1995 | Libin |
| 5,406,963 A * | 4/1995 | Adell |
| 5,447,168 A | 9/1995 | Bancroft |
| 5,460,527 A | 10/1995 | Kittelsen |
| 5,469,865 A | 11/1995 | Minneman |
| 5,490,520 A | 2/1996 | Schaefer et al. |
| 5,511,562 A | 4/1996 | Hancock |
| 5,513,656 A | 5/1996 | Boyd, Sr. |
| 5,533,524 A | 7/1996 | Minneman |
| D373,421 S | 9/1996 | Brown |
| 5,566,684 A | 10/1996 | Wagner |
| 5,584,687 A * | 12/1996 | Sullivan et al. |
| 5,586,562 A | 12/1996 | Matz |
| 5,590,643 A | 1/1997 | Flam |
| 5,592,951 A | 1/1997 | Castagnaro et al. |
| 5,624,257 A | 4/1997 | Farrell |
| 5,636,379 A | 6/1997 | Williams |
| 5,646,216 A | 7/1997 | Watson et al. |
| 5,649,534 A | 7/1997 | Briggs, III |
| 5,666,973 A | 9/1997 | Walter |
| 5,692,523 A | 12/1997 | Croll et al. |
| 5,718,243 A | 2/1998 | Weatherford et al. |
| 5,718,575 A | 2/1998 | Cross, III |
| 5,730,599 A | 3/1998 | Pak |
| 5,746,221 A | 5/1998 | Jones et al. |
| D397,442 S | 8/1998 | Kittelsen |
| 5,816,255 A | 10/1998 | Fishman et al. |
| 5,819,744 A | 10/1998 | Stoyka, Jr. |
| 5,823,193 A | 10/1998 | Singer et al. |
| 5,823,194 A | 10/1998 | Lampert |
| 5,826,581 A | 10/1998 | Yoshida |
| 5,836,761 A | 11/1998 | Belvedere et al. |

| | | | | | |
|---|---|---|---|---|---|
| 5,865,619 A | 2/1999 | Cross, III et al. | 6,036,487 A | 3/2000 | Westerman |
| 5,873,365 A | 2/1999 | Brown | 6,039,046 A | 3/2000 | Swartz et al. |
| 5,879,155 A | 3/1999 | Kittelsen | 6,068,475 A | 5/2000 | Stoyka, Jr. |
| 5,915,385 A | 6/1999 | Hakimi | 6,082,363 A | 7/2000 | Washburn |
| 5,921,240 A | 7/1999 | Gall | 6,092,524 A | 7/2000 | Barnes, Sr. |
| 5,931,164 A | 8/1999 | Kiely et al. | 6,098,627 A | 8/2000 | Kellner et al. |
| 5,947,918 A | 9/1999 | Jones et al. | 6,109,266 A | 8/2000 | Turchetti |
| 5,970,981 A | 10/1999 | Ochel | | | |
| 6,012,919 A | 1/2000 | Cross, III et al. | * cited by examiner | | |

LOW-DENSITY POLYETHYLENE DENTAL APPLIANCE AND MOUTHGUARD

BACKGROUND OF THE INVENTION

This invention relates to dental appliances and mouthguards, and more particularly to customizable dental appliances and mouthguards.

It is well known that athletes who are in contact sports wear mouthguards to protect their teeth from sharp blows as well as to protect the head and temporomandibular joint from concussion. Mouthguards are common in football, hockey, soccer, rugby, boxing, for example. Mouthguards may be considered a subgroup of dental appliances.

There is also a trend for athletes, such as body builders, weight lifters, baseball batters, golfers, football players, hockey players, and bowlers to wear dental appliances to prevent the clenching of their teeth during exertion which results in hundreds of pounds of compressed force exerted from the lower jaw onto the upper jaw. Teeth clenching also occurs in bruxing and child birthing. Clenching can result in headaches, muscle spasms, damage to teeth and injury to the temporomandibular joint as well as pain in the jaw. Thus, dental appliances have been created having posterior pads to be positioned between the upper and lower teeth to prevent clenching and damage to one's teeth and jaw structures.

It also is well known that there are dental appliances for a myriad of other uses. Splints, which look like mouthguards, are used for bleaching of teeth, while other appliances may be used to control breathing and snoring. Dentists also use appliances in administering to teeth during dentistry.

Dental appliances and mouthguards historically have been made of ethylene vinyl acetate (EVA). These devices are subject to degradation due to the user clenching and chewing on the appliance or mouthguard. EVA also has a mild ester-like odor and cannot be made clear but rather translucent to white.

Upon decomposition, EVA will break down to hazardous vinyl acetate, acetic acid, carbon monoxide and hazardous hydrocarbon oxidation products.

There is a need for dental appliances to be made of clear material for aesthetics, have low or no odor and exhibit strong flexible, tensile and impact properties.

SUMMARY OF THE INVENTION

A customizable dental appliance adapted to lie within the mouth of a person consisting of occlusal posterior pads optionally with a connective arch or a u-shaped style base with upstanding labial and/or buccal walls. The appliance is made of low-density polyethylene.

A principle object and advantage of the present invention is the appliance is made of low-density polyethylene which exhibits no odor and strong flexible, tensile and impact properties while yet being soft.

Another object and advantage of the present invention is that the customizable appliance may be made clear for aesthetics.

Another object and advantage of the present invention is that the appliance is non-hazardous.

Other objects and advantages will become obvious with the reading of the following specification and appended claims with a review of the figures.

DETAILED DESCRIPTION OF THE PREFERRED EMBODIMENT

The physical structure of dental appliances may be appreciated by reviewing FIGS. 1 through 4.

Figure 1:
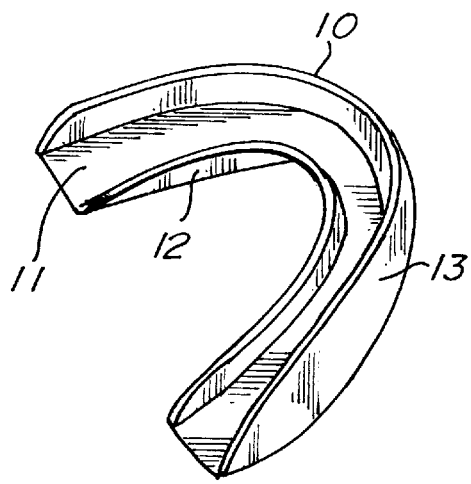
FIG. 1 is a perspective view of a traditional mouthguard suitably made of an elastomer and not designed for custom fit.
Figure 2:
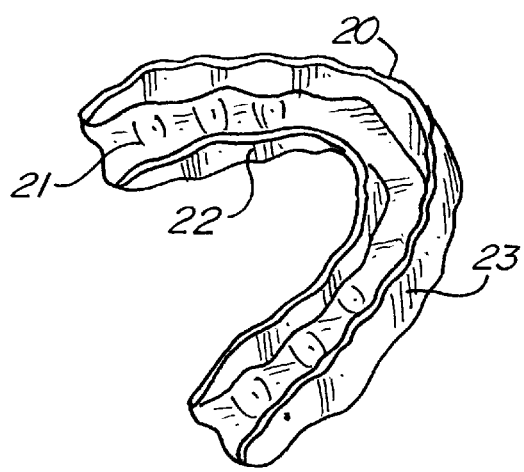
FIG. 2 is a perspective view of a custom fit mouthguard, dental appliance or splint which has been formed to the shape of the teeth and gums.

In FIG. 1, the standard non-custom mouthguard 10 generally includes a horseshoe or u-shaped base or occlusal pad 11 with a lingual wall 12 and a labial wall 13. In FIG. 2, the custom mouthguard or dental appliance 20 may have a base 21, a lingual wall 22, and a labial wall 23. Typically, the custom mouthguard 20 is placed in boiling water to soften and then fitted to the mouth for a sure-grip fit to the wearer.

Figure 3:
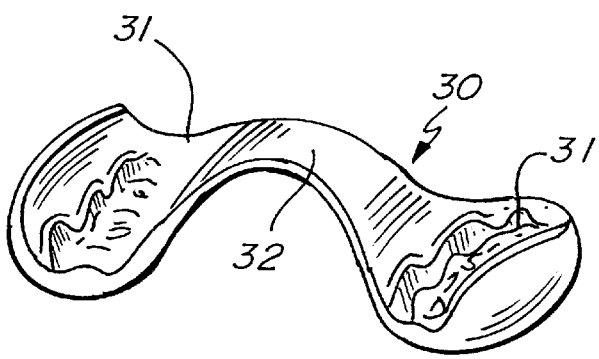
FIG. 3 is a perspective view of a dental appliance with occlusal posterior pads and a connective arch.
Figure 4:
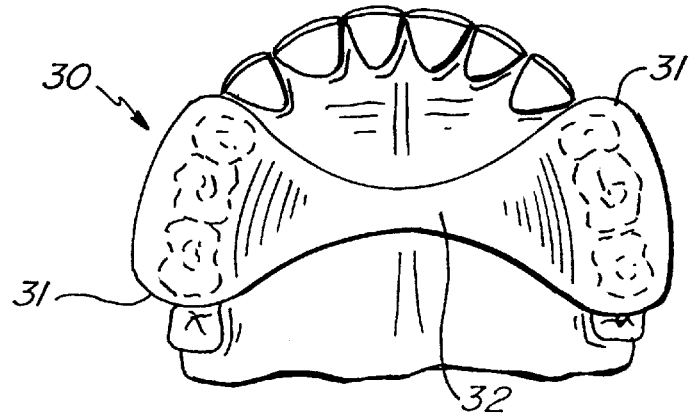
FIG. 4 is a bottom plan view of a dental appliance placed on the upper jaw.

FIGS. 3 and 4 show a typical dental appliance 30 other than a protective mouthguard 10 or 20. The appliance 30 typically includes occlusal posterior pads 31 appropriately connected by an arch 32 to assure that the appliance 30 is not swallowed by the wearer. The arch may also extend along the outside or inside of the anterior teeth.

The appliances, 10, 20 and 30 of the present invention are made of low-density polyethylene. A suitable material is EXACT® 4023 from Exxon Mobile Chemical Company of Houston, Tex. 77253-3272.

After molding into an appliance, the user simply places the appliance 10, 20 or 30 into hot water 100° to 150° for a few seconds. Thereafter, the appliance 10, 20 or 30 is removed and fitted to the user's mouth, teeth and gums just like an EVA appliance as is well known.

It is also well known that illness, infection, tooth decay and/or periodontal disease is caused by bacteria, fungus, yeast, and virus. These microbials can grow and multiply on dental appliances when the appliances are being stored between uses as well as when the appliance is actually being worn or used.

Antimicrobial substances which are non-toxic and free of heavy metal or resisting the growth of the microbials may include CHLORINATED PHENOL (e.g. 5-CHLORO-2-(2-4-DICHLOROPHENOXY)PHENOL), POLYHEXAMETHYLENE BIGUANIDE HYDROCHLORIDE (PHMB), DOXYCYCLINE, CHLORHEXIDINE, METRONIDAZOLE, THYMOL, EUCALYPOL and METHYL SALYCILATE. TRICLOSAN® from Siba Giegy of Switzerland is also available.

Incorporating an antimicrobial agent into the low-density polyethylene during the manufacture of the dental appliance 10, 20 or 30 is achieved by incorporating the agent into the synthetic polymeric master batch. The antimicrobial agent is suitably placed into the batch in a concentration as high as 10% which will permit a let-down ratio resulting in the final concentration of the antimicrobial agent and the dental appliance of about 0.005 to about 2% by weight.

By encapsulating the antimicrobial agent into the polymer batch mix, the agents survive molten temperatures approximately or above 350° F. and thus the antimicrobial agent loses none of its biocidal properties in the formation of the dental appliance 10, 20 or 30.

It is to be understood that the foregoing description and specific embodiments are merely illustrative of the best mode of the invention and the principles thereof. Various modifications and additions may be made to the present invention by those skilled in the art without departing from the spirit and scope of this invention which is to be limited only by the scope of the appended claims.

I claim:

1. A customizable athletic force absorbing mouthguard having a u-shaped base with upstanding labial and lingual walls forming a channel for the teeth of a user comprised of low-density polyethylene, further comprising an antimicrobial additive in the low-density polyethylene.

2. A customizable dental appliance having an occlusal pad to be placed on the teeth within a mouth comprised of low-density polyethylene, further comprising an antimicrobial additive in the low-density polyethylene.

* * * * *